(12) United States Patent
Phillips

(10) Patent No.: US 11,633,788 B2
(45) Date of Patent: Apr. 25, 2023

(54) CLEANING OF A 3D PRINTED ARTICLE

(71) Applicant: HS Marston Aerospace Limited, Wolverhampton (GB)

(72) Inventor: Paul Phillips, Worcestershire (GB)

(73) Assignee: HS MARSTON AEROSPACE LIMITED, Wolverhampton (GB)

( * ) Notice: Subject to any disclaimer, the term of this patent is extended or adjusted under 35 U.S.C. 154(b) by 463 days.

(21) Appl. No.: 16/824,940

(22) Filed: Mar. 20, 2020

(65) Prior Publication Data

US 2020/0217603 A1 Jul. 9, 2020

Related U.S. Application Data

(62) Division of application No. 15/591,542, filed on May 10, 2017, now Pat. No. 10,634,440.

(30) Foreign Application Priority Data

Jun. 20, 2016 (GB) ...................................... 1610728

(51) Int. Cl.
*B08B 7/02* (2006.01)
*G01V 3/10* (2006.01)
(Continued)

(52) U.S. Cl.
CPC ................ *B22F 10/20* (2021.01); *B08B 7/02* (2013.01); *B08B 9/0321* (2013.01); *B33Y 40/00* (2014.12);
(Continued)

(58) Field of Classification Search
None
See application file for complete search history.

(56) References Cited

U.S. PATENT DOCUMENTS

| 5,490,882 A | 2/1996 | Sachs et al. |
| 6,354,361 B1 | 3/2002 | Sachs et al. |

(Continued)

FOREIGN PATENT DOCUMENTS

| DE | 19524353 A1 | 1/1997 |
| WO | 9607090 A1 | 3/1996 |

OTHER PUBLICATIONS

European Search Report for Application No. 25.49.128721/02 dated Nov. 30, 2017, 9 pages.

(Continued)

*Primary Examiner* — Nicole Blan
(74) *Attorney, Agent, or Firm* — Cantor Colburn LLP

(57) ABSTRACT

The present disclosure relates to a method and apparatus for cleaning a 3D printed article, in particular a 3D printed heat exchanger. After 3D printing, an article may have internal passages formed from bonded powder and said passages may contain unbonded powder that needs to be removed before further use of/processing of the article. To remove this unbonded powder, the article is filled with a cleaning fluid and vibrated. The cleaning fluid is then pumped out of the article and past a sensor that generates a magnetic field. The sensor detects the presence of powder particles in the fluid by detecting a perturbation of the magnetic field caused by said particles. The fluid is then filtered and returned to a (Continued)

reservoir for use. The sensor may indicate the article is sufficiently clean when a detected concentration of particles in the fluid drops below a threshold.

17 Claims, 3 Drawing Sheets

(51) Int. Cl.
*G01N 15/06* (2006.01)
*B08B 9/032* (2006.01)
*G01N 27/74* (2006.01)
*B22F 10/20* (2021.01)
*B33Y 80/00* (2015.01)
*B33Y 40/20* (2020.01)
*B33Y 40/00* (2020.01)
*B22F 3/24* (2006.01)

(52) U.S. Cl.
CPC .............. *B33Y 40/20* (2020.01); *B33Y 80/00* (2014.12); *G01N 15/0656* (2013.01); *G01N 27/74* (2013.01); *G01V 3/10* (2013.01); *B22F 2003/247* (2013.01); *B22F 2999/00* (2013.01); *G01N 2015/0687* (2013.01)

(56) References Cited

U.S. PATENT DOCUMENTS

| 6,363,606 | B1 | 4/2002 | Johnson, Jr. et al. |
| 2008/0115800 | A1 | 5/2008 | Biohm |
| 2009/0314064 | A1 | 12/2009 | Augros et al. |
| 2011/0277679 | A1* | 11/2011 | Good .................. G01N 1/2202 |
| | | | 116/202 |
| 2014/0202497 | A1 | 7/2014 | Kreis et al. |
| 2015/0377571 | A1 | 12/2015 | Hiroki |
| 2016/0074940 | A1 | 3/2016 | Cote et al. |
| 2017/0363377 | A1 | 12/2017 | Phillips |

OTHER PUBLICATIONS

GB Search Report for Application No. 1610728.6, dated Dec. 16, 2016. 3 Pages.

* cited by examiner

CLEANING OF A 3D PRINTED ARTICLE

CROSS REFERENCE TO RELATED APPLICATIONS

This application is a divisional of U.S. patent application Ser. No. 15/591,542, filed May 10, 2017, which claims priority to United Kingdom Patent Application No. 1610728.6 filed Jun. 20, 2016, the entire contents of which is incorporated herein by reference.

TECHNICAL FIELD

The present disclosure relates to a method and system for cleaning a 3D printed article such as a heat exchanger.

BACKGROUND 3D printing may be used to create three-dimensional objects by printing layers of material on top of previously laid-down layers of material, such that the finished or partially-finished 3D printed product is formed of a number of thin layers of material. 3D printing is sometimes alternatively known as "additive manufacturing" or "rapid prototyping", all of which may refer to the general technique of producing 3D articles from printing multiple thin layers of the article, one on top of the other.

One 3D printing technique is to provide a movable stage beneath a computer-controlled print head. A thin flat layer of powder is spread over the stage and the printer head sprays a binder material onto specific points on the layer of powder, in accordance with a cross-section of the finished 3D printed article. The powder may be one of a variety of materials, for example a powdered metal or a powdered ceramic. The binder may be one of a variety of sprayable products, such as an adhesive. The binder reacts with the powder to form a solid blob of material at the point where the binder is sprayed. After the printer head has sprayed all the designated areas of the first layer of powder, the stage may be lowered and a new layer of loose powder is overlaid on the previous layer (that, after printing, comprises areas of loose powder and areas of bound powder). The printer head scans over the new layer of powder and deposits binder in accordance with the instructions from the controller. Thus, a second layer of the final article is completed. This process is repeated until all of the layers of the article have been printed.

Instead of using a binder from the printer head, a laser or electron beam may be used to bind the powder together. In this form of 3D printing, the laser (or electron beam) melts or welds together the metal particles caught within the beam. The beam is then scanned over the powder layer to form that cross-sectional layer of the finished or partially-finished article.

If a 3D printed article is printed using the above-described method, and the finished article contains internal passages, those passages may be filled with unbound powder. This powder must be removed to clear the passages and leave the desired article with internal passages properly formed.

After removal of the powder, the product may be complete or it may undergo further processing steps, such as heat treating.

If the powder was a metal powder, it may be desired to sinter the metal particles together to increase the strength of the article. In this process, the green (i.e. partially-completed) 3D printed article may be placed in a furnace and heated. Before heating, any excess loose powder should be removed so that the finished article properly matches the desired shape that was printed by the 3D printer. This is because a heat-treating step may fuse any unbonded powder that remains in the internal passages which may undesirably distort the internal passages. If the 3D printing process utilised a binder, then the binder may have been selected to thermally decompose during heating to allow the metal powder particles to sinter together firmly.

One type of article that may be made by 3D printing is a heat exchanger. Heat exchangers typically have a variety of internal passages for a first fluid (e.g. refrigerant) which passages may themselves surround or partially surround external passages for a second fluid (e.g. air or a second refrigerant). When a heat exchanger is constructed through 3D printing, there may be many passages, both internal and external, containing loose powder. The loose powder requires a clear access path to be properly removed, which complete heat exchanger assemblies often do not have due to the complex nature of the flow paths that have been designed for the ideal thermal performance and flow distribution. If this loose powder is not removed, it may solidify during any subsequent heat treatment and hence block the heat exchanger's flow channels thereby affecting the performance of the unit. Further, as the internal passages of the heat exchanger cannot be easily inspected it may be difficult to determine with confidence whether any cleaning process has been successful in completely removing loose powder.

Thus, there is a need for methods and systems for removing loose powder from 3D printed articles, including removing powder from internal paths within the green article or the finished article. Various methods for cleaning loose powder from internal passages have been proposed in the prior art.

US 2016/0074940 discloses a method of removing loose powder material from a cavity within a 3D printed part, wherein the cavity has at least one opening leading to the outside of the part. The part is placed on a stage and vibrated until the powder fluidizes and flows out of the cavity via the opening(s).

Such conventional methods have generally been considered satisfactory for their intended purpose. However, there is a need in the art for improved methods of clearing powder from 3D printed articles, particularly heat exchangers.

SUMMARY

According to a first aspect, the disclosure provides a method of cleaning an article comprising internal channels, the method comprising: pumping a cleaning fluid through the internal channels initially containing particles, wherein the particles have a different magnetic permeability from the cleaning fluid; passing the cleaning fluid past a sensor generating a magnetic field; and detecting the presence of particles in the fluid by detecting perturbation of the magnetic field, the perturbation being caused by the particles.

The step of detecting may comprise determining a concentration or density of particles within the fluid based on a determined degree of perturbation of the magnetic field.

The sensor may generate a magnetic field by means of an inductive coil; optionally the perturbation of the magnetic field may be detected as a change of a voltage across the inductive coil.

The method may further comprise a step of determining the article is clean when no particles are detected in the fluid or when a concentration of particles detected in the fluid has dropped below a threshold concentration, optionally wherein the threshold concentration is 5%, optionally wherein the threshold concentration is 1%.

The method may comprise filtering particles out of the fluid using a filter after the detection step. The clean fluid may be passed back to an inlet of a pump used for pumping the cleaning fluid.

The step of pumping may comprise the steps of: attaching the article to a fluid circuit; placing the article on a stage; pumping cleaning fluid into the article; vibrating the stage and thereby the article; and pumping the fluid out of the article to the sensor.

Before the step of vibrating, the method may comprise closing valves in the fluid circuit to constrain the fluid to the internal passages of the article during the vibration step.

The method may comprise a step of calibrating the sensor by: passing a clean fluid through the sensor and measuring a first voltage across the sensor; and passing a fluid containing a known concentration of particles having known magnetic permeability through the sensor and measuring a second voltage across the sensor.

The particles may be comprised of metal or ceramic.

The article may be a 3D printed article. For example, the article may be a heat exchanger. The particles may be residual particles from the 3D printing process.

The cleaning fluid may be water or water containing detergent. The cleaning fluid may optionally comprise an abrasive.

The present disclosure also provides an apparatus for cleaning an article comprising internal channels, the apparatus comprising: a pump configured to pump cleaning fluid through the internal channels to thereby remove particles from the internal channels into the fluid; and a sensor arranged to generate a magnetic field; wherein the apparatus is configured to detect, in fluid being pumped past the sensor, the presence of particles in the fluid having a different magnetic permeability than the fluid, by detecting perturbation of the magnetic field caused by the particles.

The apparatus may comprise a fluid circuit including the pump, wherein the pump defines an upstream position of the fluid circuit and is configured to pump a fluid through the circuit; wherein the fluid circuit comprises a connection downstream of the pump, the connection being configured to attach to an article comprising internal passages; and wherein the sensor is located downstream of the connection.

The apparatus may be configured to determine a density or concentration of particles within the fluid based on a determined degree of perturbation of the magnetic field.

The sensor may comprise an inductive coil for generating the magnetic field; optionally wherein the apparatus is arranged to detect a change of a voltage across the inductive coil from which the perturbation of the magnetic field is determined.

The circuit may comprise a stage configured to vibrate the article, preferably with high frequency low amplitude vibrations.

The circuit may comprise a filter downstream of the sensor for filtering particles out of the fluid.

There may be a controller connected to the sensor, the controller configured to apply a voltage to the induction coil and to detect perturbations of the voltage across the induction coil.

The sensor may comprise one or more indicators for indicating an instantaneous particle concentration in fluid passing the sensor. For example, the one or more indicators may be a series of lights, a series of LEDs, or a display screen.

The apparatus may be for cleaning an article produced by 3D printing, preferably a heat exchanger.

BRIEF DESCRIPTION OF THE DRAWINGS

Certain embodiments of the present disclosure will now be described in greater detail by way of example only and with reference to the accompanying drawings in which.

DETAILED DESCRIPTION

The following description will be given with reference to a heat exchanger that has been 3D printed from a metallic powder by laser sintering or electron beam melting (EBM). However, the method and system according to the present disclosure are applicable to other printed articles, to articles made from different materials, and to other 3D printing techniques that leave unwanted powder in the printed article.

Figure 1:
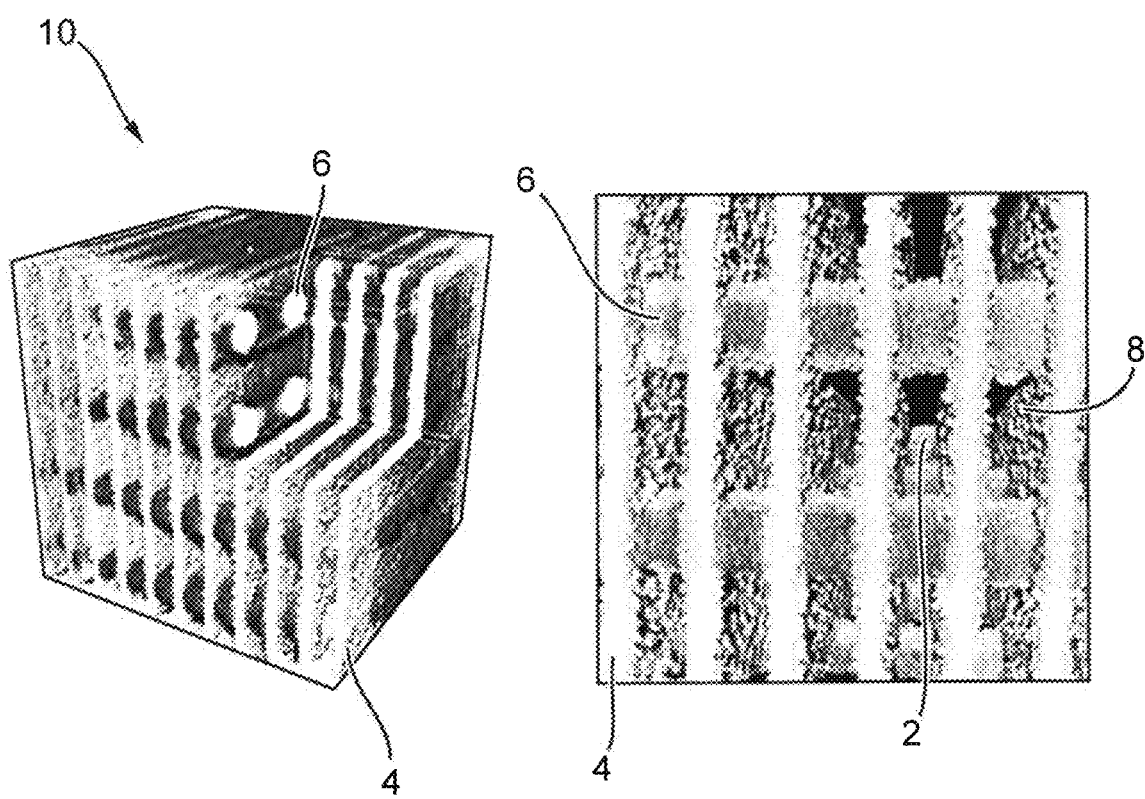
FIG. 1 shows a computerised tomography scan of a 3D printed heat exchanger.

FIG. 1 shows a computerised tomography (CAT) scan of a heat exchanger 10 (a "plate and pin" heat exchanger) that has been 3D printed by laser sintering of successive layers of loose powder. The heat exchanger 10 comprises a plurality of plates 4 held apart by pins 6. Flow channels 2 are defined between the plates 4 and around the pins 6. Loose powder 8 can be seen in FIG. 1 adhering to the plates 4 and the pins 6. In FIG. 1, the majority of the loose powder 8 that filled the heat exchanger 10 immediately after printing has already been removed. Nonetheless, some loose powder 8 may still be seen adhering to the walls of the heat exchanger in FIG. 1. However, immediately after printing the flow channels 2 will be completely filled with loose powder. This loose powder must be removed before the heat exchanger can be used.

With some 3D printed articles, it may be possible to pour out the loose powder from any internal channels or cavities. With other 3D printed articles, it may be necessary to provide further mechanical and/or chemical cleaning to remove the loose powder, especially those with complex internal passages. Loose powder that is directly adjacent bonded powder may be more difficult to remove, e.g. due to loose powder stuck among the rough surface of the bonded-powder of the article.

Figure 2:
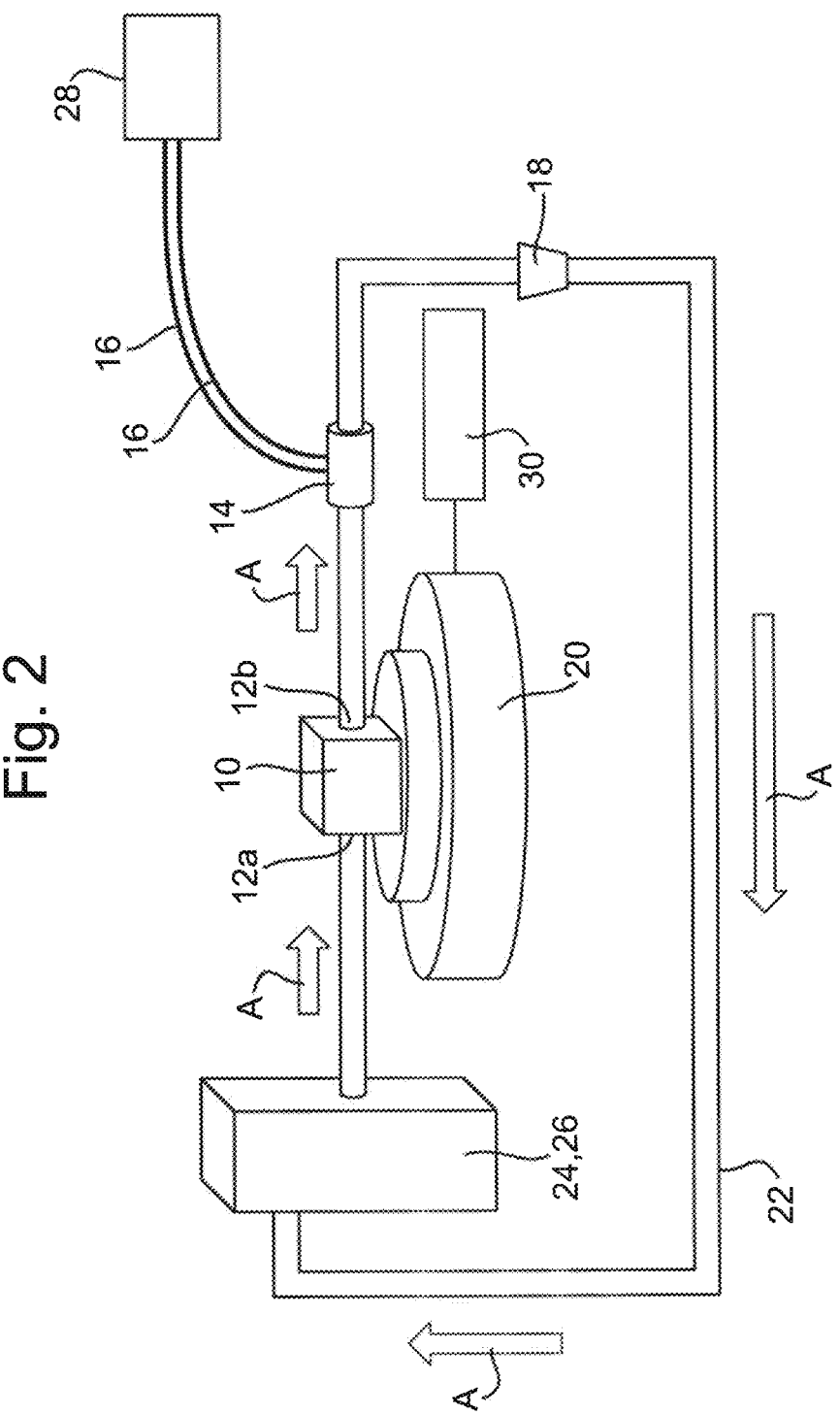
FIG. 2 shows a system for cleaning loose powder from a 3D printed article according to an example of the disclosure.

FIG. 2 shows a system for cleaning loose powder from the internal passages of a 3D printed article, for example, a heat exchanger 10. The loose powder comprises a plurality of particles, and the terms "powder" and "particles" are used interchangeably in this specification. The system may comprise a stage 20 upon which the heat exchanger 10 may be placed. The stage 20 may be configured to vibrate and may be controlled by a controller 30. The stage 20 may therefore be termed a "vibration table". The vibration may be through the use of conventional shakers or ultrasonic transducers, or other known methods of applying vibration.

The heat exchanger 10 may be connected into a cleaning circuit comprising a circuit of pipes 22. Two valves 12a, 12b may be disposed on the pipes 22 where they enter/exit the heat exchanger 10.

The system may also comprise, as part of the cleaning circuit and in serial relationship, a sensor 14, a particle filter 18, a fluid reservoir 26 and a pump 24. The sensor 14 may be an in-line particle inspection sensor that provides an indication of when the cleaning process has achieved the desired result, as described in greater detail below. In FIG. 2, the pump 24 and fluid reservoir 26 are shown in the same location. However, the pump 24 may alternatively be provided separately from the reservoir 26.

The sensor 14 may connect via wires 16 to a computer 28 arranged to process data collected via the sensor 14 and received via wires 16, and having a power supply for powering the sensor 14. The computer 28 for the sensor 14 and the controller 30 for the stage 20 may both be provided within a single computer or may be separate, as shown schematically in FIG. 2.

The filter 18 is for filtering loose powder 8 that is carried by the fluid flowing through the pipes 22.

The reservoir 26 may contain a cleaning fluid for removing loose powder 8 from the heat exchanger 10. The cleaning fluid may be water or may be water mixed with a detergent, or may be any other suitable fluid for conveying loose powder 8 out of the heat exchanger 10. The cleaning fluid may optionally contain abrasives to assist removal of loose powder, for example loose powder caught in rough surfaces of the heat exchanger walls.

In operation, the heat exchanger 10 may be removed from the 3D printer, with its flow channels 2 filled with loose powder that is to be removed. When thus filled with powder, the heat exchanger 10 will be referred to as a "green heat exchanger", to indicate that the product is not yet completed ("green" does not refer to the colour of the heat exchanger 1). After cleaning, the green heat exchanger will be referred to as "a heat exchanger".

The green heat exchanger 10 may be placed on the stage 20 and connected to the pipes 22 of the cleaning fluid circuit with valves 12a, 12b on either side of the green heat exchanger 10. The pump 24 may draw cleaning fluid from the reservoir 26 and pump it into the green heat exchanger 10.

In a first step, the fluid may be pumped into the green heat exchanger 10 until fluid first reaches the downstream valve 12b, i.e. the valve 12b on the far side of the green heat exchanger 10 from the pump 24. At this point, both valves 12a, 12b may be closed and the pump 24 deactivated.

The stage 20 is then vibrated under the direction of the controller 30. The vibration may be low-amplitude high-frequency vibrations. Using low-amplitude vibrations may avoid damage to the article being cleaned. The vibration may be at a single frequency or may be varied over a range of frequencies, and may be applied for a predetermined duration. The vibration may loosen the loose particles 8.

The most appropriate frequencies and amplitudes for the cleaning process will be dependent on the part design, material type and the size of powder particles being removed from the part. By way of non-limiting example, a frequency range of 20-400 kHz may be used. For more robust components and those containing heavier loose particles of powder, frequencies below 80 kHz may be appropriate. For more delicate components and components for which a higher level of cleanliness is required, frequencies above 80 kHz may be appropriate. A mix of these processes may be useful, for example starting with low frequency vibrations to remove larger particles and then switching to high frequency for the removal of smaller (e.g. submicron) particles.

After the vibration step, the valves 12a, 12b may be opened and the pump 24 restarted. The fluid is pumped out of the green heat exchanger through pipes 22 along a path A, carrying with it some of the loose powder 8. The fluid flows though pipes 22 past the sensor 14 and onwards into the filter 18 where the powder is partly or entirely filtered out of the fluid. The filtered fluid may then continue to flow through the pipes 22 back into the reservoir 26 ready to be used again. The sensor 14 may output a signal indicative of the particle density of loose powder suspended in the fluid flowing through the sensor. As described in more detail below, the sensor may thus be used to determine the progress of the cleaning process and when it is finished, i.e. when the article is sufficiently clean.

In one example, after the fluid has completed a single circuit of the system (i.e. from the reservoir 26, via the pump 24, green heat exchanger 10, sensor 14, filter 18, and back to the reservoir 26) the process may restart, with the pump 24 filling up the green heat exchanger 10, vibrating the heat exchanger, and then pumping the fluid out of the green heat exchanger 10 again. Alternatively, after the first vibration step, the pump may continuously draw fluid from the reservoir and pump it through the green heat exchanger until the green heat exchanger 10 is deemed to be clean (as described below). In this continuous example, the vibration may be applied continuously, intermittently, or not applied at all after the first vibration stage.

Figure 3:
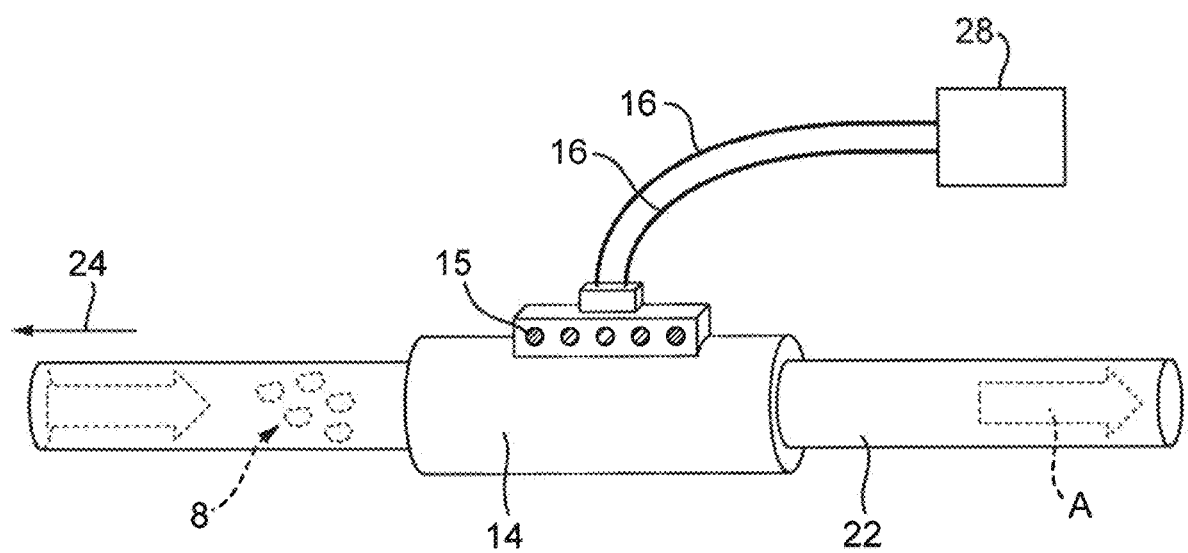
FIG. 3 shows a sensor for detecting a concentration of particles in a fluid according to an example of the disclosure.

The sensor 14 is shown in more detail in FIG. 3. The sensor 14 may comprise an inductive coil (not shown) wrapped around the pipe 22. The pipe 22 may be made from a non-ferrous material or from a ferrous material. The computer (controller) 28 may provide a voltage to the inductive coil which generates a magnetic field that extends through the portion of the pipe 22 within the coil and thus through the fluid within the pipe 22. The particle-containing fluid will perturb (disrupt) the magnetic flux (field) generated by the inductive coil, and this perturbation can be measured as a change in the voltage across the coil.

Provided that the particles have a different magnetic permeability from the fluid, different quantities of particles in the fluid will perturb (disrupt) the magnetic field (when compared to the original magnetic field applied) to different degrees. Thus, the perturbation can be used as a measure of the quantity of particles present in the fluid, and therefore how clean it must be.

For example, the voltage across the inductive coil may change depending upon the concentration of particles 8 within the fluid, this voltage may be measured and the data provided to the computer 28. The computer may be programmed to use this measured voltage together with data of the magnetic permeability of the particles and fluid, to thereby estimate the concentration of particles within the fluid.

The change in magnetic flux in the inductive coil may be empirically related to the density of particles in the fluid flowing through the sensor. It is anticipated that the change in magnetic flux in the induction coil will be proportional to the density of particles in the fluid flowing through the sensor:

$$\Delta B \propto D_P$$

where: B=magnetic flux
$D_P$=density or concentration of particles

The relationship may be determined through experimentation. Varying particle densities may be introduced to a fluid flow and the corresponding magnetic flux changes measured. Plotting these against each other may allow the necessary relationship to be extracted from the resulting graph. The relationship may be different depending on whether the particles comprise ferrous or non-ferrous material.

The sensor 14 may be calibrated by comparing the sensor's output when clean fluid (i.e. powder-free) is pumped through the sensor 14, with the sensor's output when fluid containing a known particle concentration is pumped through the sensor 14.

Figure 4:
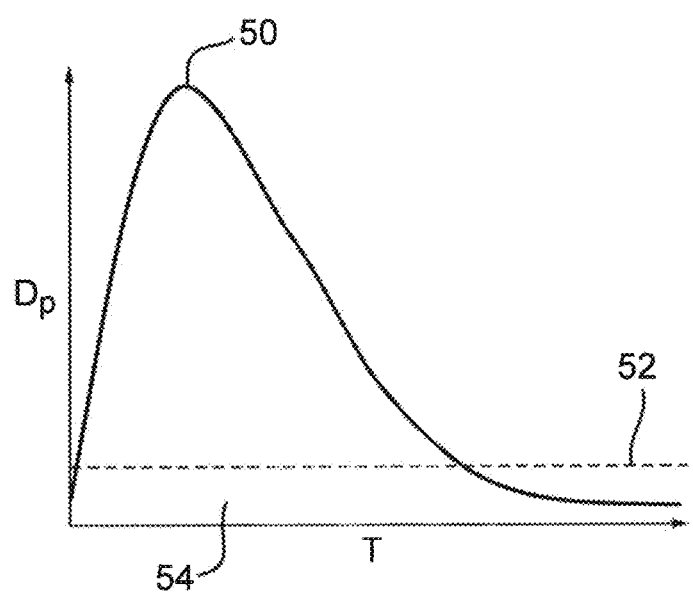
FIG. 4 shows a graph of particle-concentration against time, as detected by the sensor.

FIG. 4 shows a graph of particle concentration $D_p$ within the fluid against time T during a cleaning process. The time T may either be measured continually, e.g. in seconds, or may be measured in number of cycles of the cleaning process if discreet steps are used. The units of $D_p$ are arbitrary and may correspond to a density or to a concentration (and these terms are generally used interchangeably in this specification). For example, $D_p$ may be measured as: the number of particles per unit volume of fluid; the number of particles per unit mass of fluid; the weight of particles per unit volume of fluid (generally termed "density"); or the weight of particles per unit weight of fluid. Where the units of measurement of the particles match the units of measurement of the fluid, the result may be expressed as a percentage and termed "concentration". For example, if there is 1 g of particles carried by 100 g of fluid, it may be said that the concentration of particles is 1%.

The concentration of particles detected by the sensor 14 is shown by a line 50 on the graph. A threshold concentration of particles can be chosen, depending on application, as indication that a sufficient amount of loose powder has been removed from the green heat exchanger 10 by the cleaning process and thus the article is sufficiently clean. After the cleaning process has run for a number of cycles or for a certain time, the detected particle concentration 50 may drop below the threshold concentration 52. This is because as cleaning is being performed powder is gradually removed from the heat exchanger, and thus the amount of loose powder 8 remaining in the heat exchanger 10 reduces, so the amount of loose powder 8 that is carried out with the fluid during further cleaning reduces. I.e., the maximum possible concentration of particles in the fluid drops because the particle concentration is now limited by the amount of remaining loose power 8 in the heat exchanger. Thus, the system may be configured to detect when the particle content of the fluid is at or below the threshold concentration, and thereby determine that the article is now clean. The system may be configured to stop the cleaning process at this point. The threshold concentration of particles in the fluid below which the article is considered clean may be e.g. 5%, 2% or 1%. The concentration (or density) may be measured in any of the manners described above.

The particle concentration Dp in the fluid may be correlated with the amount of loose powder 8 remaining in the heat exchanger 10. Calibration tests may be performed to find such a correlation. For example, when the particle concentration Dp drops below the threshold, it may be determined that there is a known, limited, amount of loose powder 8 remaining in the heat exchanger 10, or in other words that a certain percentage of the original quantity of powder has been removed. As one non-limiting example, the threshold concentration of particles in the fluid may be set such that, when the threshold is reached, 90%, or 95%, or 99% of the loose powder within the article has been removed.

The sensor 14 may be calibrated to detect a particular concentration of particles within the fluid. For example a first voltage across the induction coil may be associated with a first particle concentration within the fluid (e.g. a high particle concentration) and a second voltage across the induction coil may be associated with a second particle concentration within the fluid (e.g. a low particle concentration) and a third voltage across the induction coil may be associated with a clean fluid containing substantially no particles from the 3D printed article (e.g. the threshold concentration has been reached).

The sensor 14 may further comprise a visual indicator 15 that indicates the detected particle concentration 50 within the fluid. The visual indicator 15 may comprise a series of LEDs having different colours, wherein different LEDs are lit depending on the detected concentration. For example, a red LED may indicate a high concentration 50 of particles 8, one or more orange/yellow LEDs may indicate an intermediate concentration 50 of particles, and a green LED may indicate that a particle concentration 50 has dropped below the threshold concentration 52. The visual indicator 15 may provide a quick indication to an operator as to the progress of the cleaning process.

A larger difference in the magnetic permeability of the powder 8 compared to the cleaning fluid may be more easily detected by the sensor 14. This may be the case if the heat exchanger is formed from a powder containing Ni, Al, or Fe or a mixture thereof and/or alloys thereof. However, the sensor may be calibrated to other materials, such as non-ferrous metals and ceramics.

As described in detail above, the method of the present disclosure may involve one or more of the following steps:
1) Place the 3D printed article on a stage;
2) Connect the article into a circuit of pipes;
3) Pump cleaning fluid via the pipes into the article until a desired quantity is provided e.g. the article is full;
4) Close valves at the entry and exit of the article and shut off the pump;
5) Vibrate the article on the stage;
6) Open the valves and restart the pump;
7) Pump the fluid out of the article through the pipes and past a sensor;
8) Detect a concentration of particles within the fluid with the sensor;
9) Filter the particles out of the fluid downstream of the sensor;
10) Return the filtered fluid to a reservoir for the pump.

As described above, the step of detecting a concentration of particles may be performed by a sensor comprising an induction coil having a voltage. The magnetic field produced by the induction coil may interact with, e.g. be perturbed by, the particles in the fluid, provided the magnetic permeability of the particles is different from the magnetic permeability of the fluid. This perturbation may be indicative of the particle concentration within the fluid and may be detected by the sensor. The sensor may output a signal indicative of a particle concentration within the fluid.

After the fluid has been returned to the reservoir, the process may repeat steps 3 to 10 until a concentration of particles drops below a threshold. The number of cycles required before the article is sufficiently clean may depend on the length and configuration of the internal passages.

Alternatively, the pump may be operated to pump a continuous flow of cleaning fluid through the article. The reservoir may be provided with a sufficient quantity of fluid to enable continuous operation from start-up, or continuous operation may not be possible until the reservoir starts to be replenished with returned fluid. During this continuous flow, the vibration may optionally be applied continuously or intermittently or not at all. Continuous flow may continue until a concentration of particles detected by the sensor drops below a threshold. The amount of time required before the article is sufficiently clean may depend on the length and conformation of the internal passages.

The particle concentration at a given moment may be displayed by one or more indicators on the sensor. For example, LEDs or an LCD display disposed on the sensor.

By providing an indication of the particle concentration in the cleaning fluid, and a determination of when a threshold concentration is reached, the present disclosure thereby enables the user to determine if and when the article is sufficiently clean, and thus if and when the cleaning process can be stopped. This ensures both that the article is clean enough for use, and also avoids unnecessary continuation of the cleaning process. This is particularly useful with articles such as heat exchangers, of which the internal channels are difficult to inspect, since the system can provide the user with confidence that the cleaning process has been successful in removing unfused powder. The method may provide an accurate and sophisticated way of measuring particle density and extent of a cleaning process.

The above description is of specific examples only and it will be appreciated that variations may be made to the embodiments without departing from the broad scope of the disclosure as defined by the following claims.

The invention claimed is:

1. An apparatus for cleaning an article comprising internal channels, the apparatus comprising:
   a pump configured to pump cleaning fluid through the internal channels to thereby remove particles from the internal channels into the fluid;
   a sensor arranged to generate a magnetic field, wherein the sensor is configured to detect, in fluid being pumped past the sensor, the presence of particles in the fluid having a different magnetic permeability than the fluid, by detecting perturbation of the magnetic field caused by the particles; and
   a fluid circuit including the pump, wherein the pump defines an upstream position of the fluid circuit and is configured to pump a fluid through the circuit;
   wherein the fluid circuit comprises a connection downstream of the pump, the connection being configured to fluidly attach to an article comprising internal passages;
   wherein the sensor is located downstream of the connection;
   wherein the fluid circuit comprises a stage configured to vibrate the article;
   wherein the fluid circuit comprises valves configured to constrain fluid to the internal channels of the article when the article is vibrated on the stage.

2. An apparatus as claimed in claim 1, wherein the apparatus comprises a controller, wherein the controller is configured to determine a density or concentration of particles within the fluid based on the degree of perturbation of the magnetic field detected by the sensor.

3. An apparatus as claimed in claim 2, wherein the controller is configured to determine the article to be clean when no particles are detected in the fluid or when a concentration of particles detected in the fluid is below a threshold concentration.

4. An apparatus as claimed in claim 3, wherein the threshold concentration is 5%.

5. An apparatus as claimed in claim 1, wherein the sensor comprises an inductive coil for generating the magnetic field.

6. An apparatus as claimed in claim 5, wherein the sensor is arranged to detect a change of a voltage across the inductive coil from which the perturbation of the magnetic field is determined.

7. An apparatus as claimed in claim 6, further comprising a controller connected to the sensor, the controller configured to apply a voltage to the inductive coil and to detect perturbations of the voltage across the inductive coil.

8. An apparatus as claimed in claim 1, wherein the circuit comprises a circuit of pipes and the valves are disposed on the pipes.

9. An apparatus as claimed in claim 8, wherein a valve is disposed on a pipe at a point where it is configured to connect to the article and supply fluid to enter the article and wherein a valve is disposed on another pipe at a point where it is configured to connect to the article and receive fluid exiting the article.

10. An apparatus as claimed in claim 1, wherein the stage is the configured to vibrate the article with high frequency low amplitude vibrations.

11. An apparatus as claimed in claim 1, wherein the stage is configured to vibrate the article at a frequency in the range of 20 to 400 kHz.

12. An apparatus as claimed in claim 1, wherein the stage is configured to vibrate at a first frequency to loosen particles and vibrate at a second frequency higher than the first frequency to loosen particles smaller than those loosened by the first frequency.

13. An apparatus as claimed in claim 1, wherein the circuit comprises a filter downstream of the sensor for filtering particles out of the fluid.

14. An apparatus as claimed in claim 1, wherein the sensor comprises one or more indicators for indicating an instantaneous particle concentration in fluid passing the sensor.

15. An apparatus as claimed in claim 14, wherein the one or more indicators are a series of lights, a series of LEDs, or a display screen.

16. An apparatus as claimed in claim 1, wherein the article is a three-dimensional printed heat exchanger.

17. An apparatus as claimed in claim 16, wherein the particles are residual particles from the 3D printing process.

* * * * *